(12) United States Patent
Prokop et al.

(10) Patent No.: US 7,888,103 B2
(45) Date of Patent: Feb. 15, 2011

(54) METHOD OF DETOXIFICATION OF YPERITE BY USING HALOALKANE DEHALOGENASES

(75) Inventors: Zbynek Prokop, Brno (CZ); Jiri Damborsky, Brno (CZ); Frantisek Oplustil, Brno (CZ); Andrea Jesenska, Brno (CZ); Yuji Nagata, Sendai (JP)

(73) Assignee: Masarykova Univerzita, Brno (CZ)

( * ) Notice: Subject to any disclaimer, the term of this patent is extended or adjusted under 35 U.S.C. 154(b) by 433 days.

(21) Appl. No.: 11/916,144

(22) PCT Filed: Jun. 1, 2006

(86) PCT No.: PCT/CZ2006/000036

§ 371 (c)(1),
(2), (4) Date: Nov. 30, 2007

(87) PCT Pub. No.: WO2006/128390

PCT Pub. Date: Dec. 7, 2006

(65) Prior Publication Data

US 2008/0248557 A1 Oct. 9, 2008

(30) Foreign Application Priority Data

Jun. 3, 2005 (CZ) .................................. 2005-352

(51) Int. Cl.
*C12N 9/00* (2006.01)
*C12N 9/14* (2006.01)
*C12N 1/20* (2006.01)
*C12N 15/00* (2006.01)
*A62D 3/00* (2007.01)
*C07H 21/04* (2006.01)

(52) U.S. Cl. .................... 435/262.5; 435/183; 435/195; 435/252.3; 435/320.1; 536/23.2

(58) Field of Classification Search ....................... None
See application file for complete search history.

(56) References Cited

FOREIGN PATENT DOCUMENTS

WO   WO 01/56380   8/2001

OTHER PUBLICATIONS

Chica et al. Curr Opin Biotechnol. Aug. 2005;16(4):378-84.*
Sen et al. Appl Biochem Biotechnol. Dec. 2007;143(3):212-23.*

* cited by examiner

*Primary Examiner*—Christian L Fronda
(74) *Attorney, Agent, or Firm*—Notaro, Michalos & Zaccaria P.C.

(57) ABSTRACT

The method of detoxification of yperite—bis(2-chloroethyl) sulfide—by the use of a haloalkane dehalogenases or their compositions, the method of preparation of dehalogenationating enzymes and of decontamination compositions which contains at least one wild type and/or modified haloalkane dehalogenase (EC 3.8.1.5) as an chemically active component. The preferred dehalogenases are LinB from *Sphingomonas paucimobilis* UT26, DhaA from *Rhodococcus rodochrous* NCIMB 13064, DmbA from *Mycobacterium bovis* 5033/66. Decontamination is utilizable for detoxification of yperite from the surfaces of instrumentality, constructional objects, human or animal skin and elements of environment by the treatment of yperite with the detoxification composition according the invention at +10° C. to +70° C., preferably at about +40° C. and pH from 4 to 12.

8 Claims, 1 Drawing Sheet

METHOD OF DETOXIFICATION OF YPERITE BY USING HALOALKANE DEHALOGENASES

FIELD OF THE INVENTION

Figure 1:
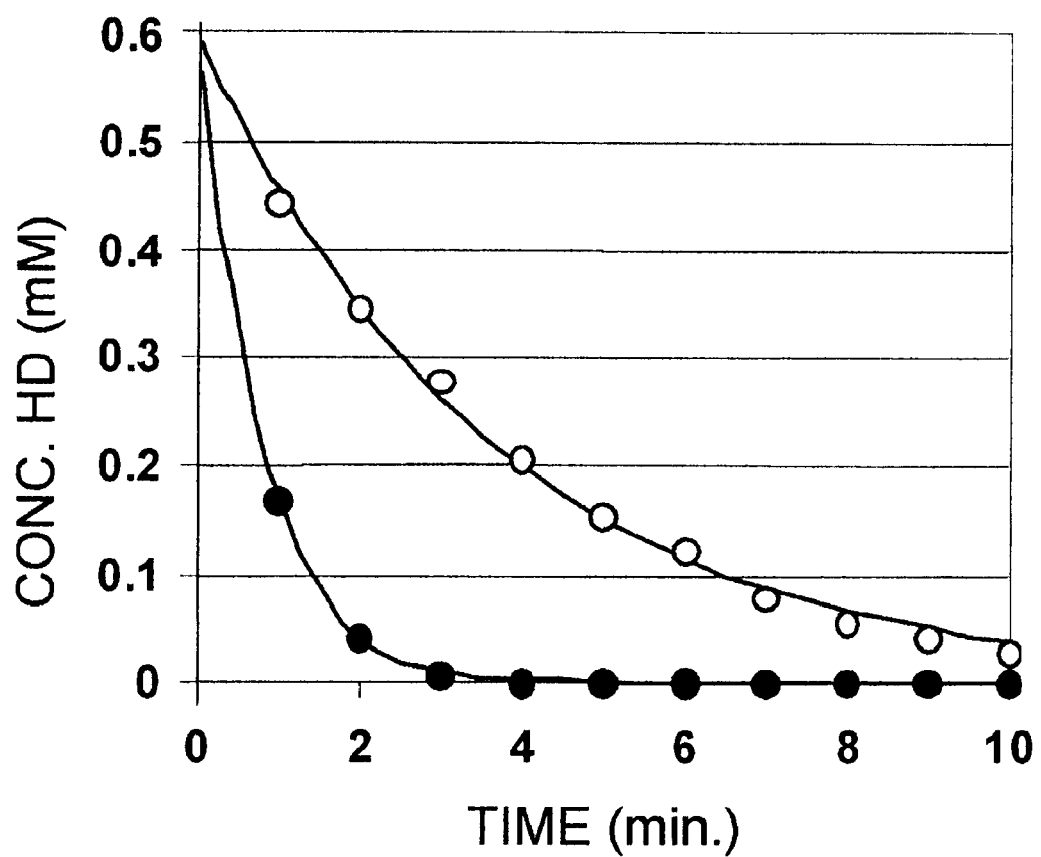

This invention relates to method for detoxification of yperite 2,2'-dichlorodiethylsulfide—by using haloalkane dehalogenases (Enzyme Commission number EC 3.8.1.5) as a primary, chemically active component of decontamination compositions. Decontamination compositions are designated for detoxification of yperite (2,2-dichlorodiethylsulfide) on the surface of military hardware, transportation, industrial and agricultural hardware, technical devices and constructional objects (hereafter instrumentation), human or animal skin and elements of environment (water, soil, sediments and air), that are contaminated by this highly toxic blistering substance.

STATE OF THE ART

At the present time, decontamination compositions are being used in the armed forces, civil defense troops, fire services and rescue forces, that exhibit high unit consumption and undesirable aggressiveness on material, because their chemically active components are stechiometric agents, that are gradually consumed during their reaction with yperite. Their application on instrumentation leads to depreciation of decontaminated material or surfaces by corrosion and if these compositions get into soil or water, it endangers environment.

There have been described enzymes in the literature that exhibit activity against highly toxic organophosphorous (neural) substances, called organophosphate hydrolases, OPA anhydrases or DFPases. As the only example of biological detoxification of blistering yperite (2,2'-dichlorodiethylsulfide), the use of bacteria species *Rhodococcus rhodochrous* IGTS8 (ATCC 53968) was mentioned in the art so far, which has the ability to utilize a chemical analog of yperite 2-chloroethyl-ethylsulfide as the only source of carbon for its growth [Kilbane, J. J., and Jackowski, K. (1996) *J. Chem. Tech. Biotechnol.* 65, 370-374]. Detoxification activity of bacteria species *Rhodococcus rhodochrous* IGTS8 (ATCC 53968) is based on splitting the S—C bond in the molecule. The application of the enzyme splitting C—S bond in a nontoxic product of hydrolysis, thiodiglycol, has been published [Harvey, S., DeFrank, J. J., Valdes, J. J., Kamely, D, and Chakrabarty, A. M., (1990) *Proceedings: Biotechnology-Biodegradation Workshop Symposium by US Army Research Office*, 47-58; Kilbane, J. J., (1990) *Resources Conserv. and Recycl.* 3, 69-79].

Haloalkane dehalogenases are enzymes that are able to remove halogen from halogenated aliphatic compound by a hydrolytic replacement, forming the corresponding alcohols [Janssen, D. B. Pries, F., and Van der Ploeg, J. R. (1994) *Annual Review of Microbiology* 48, 163-191]. Hydrolytic dehalogenation proceeds by formal nucleophilic substitution of the halogen atom by hydroxyl ion. Structurally, haloalkane dehalogenases belong to the α/β-hydrolase fold superfamily [Ollis, D. L., Cheah, E., Cygler, M., Dijkstra, B., Frolow, F., Franken, S. M., Harel, M., Remington, S. J., Silman, I., Schrag, J., Sussman, J. L., Verschueren, K. H. G., and Goldman, A. (1992) *Protein Engineering* 5, 197-211]. Haloalkane dehalogenases contain a nucleophile elbow [Damborsky, J. (1998) *Pure and Applied Chemistry* 70, 1375-1383] that belongs to the most conserved structural features of the α/β-hydrolase fold. Another highly conserved region in haloalkane dehalogenases is the central β-sheet that is flanked on both sides by α-helixes that form hydrophobic core of the main domain. The main domain carries the catalytic triad: aspartic acid-histidine-aspartic acid/glutamic acid (Asp-His-Asp/Glu). The second domain is solely consisting of α-helixes and is placed like a cap on top of the main domain. The interface between the main and the cap domain forms the active site of the enzyme. Whereas there is significant similarity between main domains, the sequence and structure of the cap domain varies significantly in different haloalkane dehalogenases. It is supposed, that character and structure of the cap domain essentially determine the substrate specificity [Pries, F., Van den Wijngaard, A. J., Bos, R., Pentenga, M., and Janssen, D. B. (1994) *Journal of Biological Chemistry* 269, 17490-17494; Kmunicek, J., Luengo, S., Gago, F., Ortiz, A. R., Wade, R. C., and Damborsky, J. (2001) *Biochemistry* 40, 8905-8917].

BRIEF DESCRIPTION OF THE DRAWING

In the drawing:

FIG. 1 is a graph plotting concentration against time for conversion of yperite in accordance with the invention.

DESCRIPTION OF THE INVENTION

The disadvantages of the above mentioned existing decontamination compositions containing stechiometric agents, are to the great extent overcome by preparations in accordance with the present invention comprising a catalyst of hydrolytic detoxification of yperite (2,2'-dichlorodiethylsulfide), which is enzyme or mixture of enzymes haloalkane dehalogenases. The basic and active component of the compositions is at least one wild type or modified enzyme of the haloalkane dehalogenase family (EC 3.8.1.5). The present invention provides a method of detoxication of yperite by the use of haloalkane dehalogenases which comprises hydrolytic dehalogenation of yperite, wherein yperite is treated with the detoxification composition containing one or more wild type or modified haloalkane dehalogenases and is thereby converted to the non-toxic product thiodiglycol.

Haloalkane dehalogenase is expressed in the natural producer or in a heterologous host organism, e.g. in bacteria *Escherichia coli*, or in yeast *Pichia pastoris*. The enzyme used can be comprised in non-living or living cells, in the form of crude extract or purified protein. As an enzyme for the dehalogenase composition at least one haloalkane dehalogenase selected from the family of enzymes EC 3.8.1.5 is used, e.g. haloalkane dehalogenase DhaA from *Rhodococcus rhodochrous* NCIMB 13064, DmbA from *Mycobacterium bovis* 5033/66 or LinB from *Sphingomonas paucimobilis* UT26.

Haloalkane dehalogenases constitute an important group of enzymes that are able to cleave the halogen-carbon bond in halogenated aliphatic compounds. They exhibit a broad substrate specificity including haloalkanes, halocycloalkanes, haloalkenes, haloethers and haloalcohols. The mechanism of dehalogenation is based on the nucleophilic attack to the carbon atom to which the halogen is bound and proceeds to cleavage of halogen ion and formation of alkyl-enzyme intermediate. The intermediate is subsequently hydrolyzed, yielding the corresponding alcohol, halogen ion and proton. The enzyme haloalkane dehalogenase transforms yperite into non-toxic bis(2-hydroxyethyl)sulfide by hydrolytic dehalogenation.

In the decontamination compositions haloalkane dehalogenase can be in crude extract or purified, immobilized on a carrier material, free in aqueous solution, in a monophasic organic or aqueous solution or in organic/aqueous biphasic systems. Enzymes can be immobilized by absorption on the inorganic or organic carrier material (such as: Celite, activated charcoal, aluminium oxide, cellulose, synthetic resins or Sephadex which is based on synthetically derived polysaccharide (dextran) or covalent attachment onto the surface of organic material (such as: cellulose, dextran, starch, chitin, agarose) or inorganic material (such as: porous glass), or synthetic polymeric carrier material (such as: VA-Epoxy Biosynt, Eupergit): The enzyme may be immobilized also by cross-linking (linkage to each other) or entrapping enzyme into a solid matrix or a compartment confined by a membrane.

The enzyme haloalkane dehalogenase may be dissolved, crystalline, lyophilized or precipitated. The liquid medium is an organic solvent, a mono-phasic aqueous solution of organic solvent or bi-phasic system consisting of organic solvent and water. The enzyme can be confined to a restricted area, where it remains catalytically active—entrapped into a solid matrix or into compartments restricted by a membrane. Enzymes may be entrapped into a biological matrix, e.g., agar gel, alginate gel, κ-carragenan. The enzyme can be entrapped also to inorganic stable matrices, e.g., silica gel. A tight network that is able to carry isolated enzyme can be obtained by polymerization of synthetic monomers, e.g., polyacrylamide, in the presence of the enzyme. Depending on the immobilization technique, the properties of the enzyme such as catalytic rate, stability and binding affinity may be significantly altered. The hydrolytic detoxification of yperite catalysed by the enzyme can be performed in the temperature range of 10-70° C. with reaction optimum of about 40° C.

Additional components are aqueous buffer systems (e.g., phosphate buffer, tris-sulfate buffer, glycine buffer, acetate buffer or citrate buffer) which stabilize the neutral pH being close to optimum interval of 7.0-8.5. The pH activity profile is broader and allows pH interval from 4 to 12 while maintaining a reasonable activity. Other additional components are surfactants or organic solvents that facilitate dissolving of yperite in aqueous solvents. Addition of water-miscible organic solvents, e.g., methanol, tert-butanol, acetone, dioxane, acetonitrile, dimethyl formamide, dimethyl sulfoxide, tetrahydrofuran, 3-methyl-3-pentanol and pyridine, can be used at concentration up to 70% of the total volume depending on the enzyme stability.

Decontamination compositions based on haloalkane dehalogenases can consist of two macroscopic phases, namely the aqueous phase containing the dissolved enzyme and a second phase consisting of organic solvents, partially water soluble or insoluble in water, e.g., ethyl acetate, diethyl ether, methyl tert-butyl ether, cyclohexanol, n-propylacetate, ethyl chloroacetate, bis(2-chloroethyl)ether, isopropyl acetate, butyl acetate, isobutyl acetate, hexanol, isoamyl acetate, n-amyl acetate, toluene, octanol, isoheptane, n-butyl ether, cyclohexane, 2-methylpentane, n-hexane, methylcyclohexane and n-octane. Organic phase enhances solubility of yperite in the decontamination composition which penetrates into water phase. The reaction takes place in aqueous phase, where the enzyme is in natural environment and is not in direct contact with organic solvent, where the most of dissolved yperite is located. The transfer of reactant and product between the two phases, reactant to the enzyme, product from the enzyme, can be increased by enlarging the surface between the two phases (producing a fine dispersion) or by stirring. The bulk water can be replaced by addition of water immiscible organic solvent. The enzyme is then suspended in a monophasic organic solvent. The optimum catalytic activity of the enzyme in organic solvent can be obtained by adjustment and maintenance of the water content. This can be conventionally obtained by a pair of salt/hydrate, e.g., $CaCl_2.H_2O/2\ H_2O$, NaI anh./2 $H_2O$, $Na_2HPO_4$ anh./2 $H_2O$, NaOAc anh./3 $H_2O$, NaBr anh./2 $H_2O$, $Na_4P_2O_7$ anh./7 $H_2O$, $Na_2HPO_4.2\ H_2O/7\ H_2O$, $Na_2SO_4$ anh./10 $H_2O$, $Na_2HPO_4.7\ H_2O/12\ H_2O$, that are added to the solvent and function as a water content buffer. The enzyme solubility in lipophilic organic solvents can be modified by covalent attachment of the amphiphatic polymer polyethylene glycol to the surface of enzyme. Linkage of the polymer chain onto the enzyme surface is achieved by reaction of ϵ-amino groups of lysine residues with "linker", e.g., cyanuric chloride. Protein stabilizers such as polyalcohols, e.g., sugar alcohols or glycerol, inactivated proteins, e.g., bovine serum albumin, or polymers, which show a certain structural resemblance with water, e.g., polyethylene glycol, polyvinyl alcohol, can be added to the reaction medium to enhance the enzyme stability.

Haloalkane dehalogenases used according to this invention can be further produced by means of rational design based on structural analysis, e.g., protein crystallography, nuclear magnetic resonance and circular dichroism spectroscopy, and biochemical characterization, e.g., steady-state kinetics, transient-state kinetics, stability and thermo stability assays, spectroscopic analyses and the like, followed by computer modelling, e.g., sequence comparisons, phylogenetic analysis, homology modelling, molecular docking, molecular mechanics, molecular dynamics, quantum mechanics and multivariate statistics, and DNA mutagenesis, e.g., cassette mutagenesis, site-directed mutagenesis, chemical mutagenesis, error-prone PCR, site saturation mutagenesis, ensemble mutagenesis, recursive ensemble mutagenesis, scanning saturation mutagenesis, mutator strains, etc. The procedure includes altering at least one amino acid residue of the haloalkane dehalogenase with another amino acid residue or recombining two or more members of the haloalkane dehalogenases to obtain a modified enzyme with improved efficacy. Modified nucleic acids can be introduced into a cell, in which they can be expressed to provide an altered haloalkane dehalogenase.

Advantages of decontamination compositions with haloalkane dehalogenases are that a) It possesses desired detoxification activity towards the yperite, which is homogeneously dissolved in aqueous solutions with pH in the range from 4 to 12 (with the neutral optimum of pH 7.0 to 8.5) at the temperature range +10 to +70° C. with reaction optimum at about +40° C.
b) A low initial concentration ($1\times10^{-6}$ mol.l$^{-1}$) is sufficient to attain desired reaction rate that means a satisfactory level of detoxification in about 15 to 30 minutes, whereas the upper limit of the enzyme concentration is $1\times10^{0}$ mol.l$^{-1}$.
c) It exhibits catalytic activity, i.e. it remains unexhausted during reaction, which brings cost reduction in logistic area.
d) It doesn't exhibit chemical aggressiveness against common construction materials and components of technique that resist the affect of neutral aqueous, corrosively non-aggressive decontamination compositions (aqueous suspensions, foams, emulsions or micro-emulsions).
e) It doesn't exhibit any toxicity and is degradable in environment

DESCRIPTION OF THE EXEMPLARY EMBODIMENT

The enzyme is prepared by homologous expression in native producer or by heterologous expression in a host organism, e.g., bacterium *Escherichia coli* or yeast *Pichia*

*pastoris*. According to the invention, the enzyme present in living or non-living cells is used in the form of crude extract or purified protein.

Example 1

To overproduce wild type of enzyme haloalkane dehalogenase LinB from *Sphingomonas paucimobilis* UT26 (Sequence 1 and 2) the corresponding gene was cloned in the pPICZαA expression vector. Cloned plasmids were then transferred into *Pichia pastoris* GS115. *Pichia pastoris* GS115 was then cultured at 28° C. in growth medium (1 weight % of yeast extract, 2 weight % of peptone, $4 \times 10^{-5}$ weight % of Biotine and 1 weight % of casamino acid in 100 mM potassium phosphate buffer, pH 6.5). The induction of the enzyme synthesis was initiated by addition of 0.7 volume % of methanol when the culture reached an optical density of 2 at 600 nm. After induction the culture was incubated at 28° C. for 10 h and then harvested. Ammonium sulfate was added to supernatant to a final concentration of 75% of saturation. Solution was stirred 30 min until the added ammonium sulfate was dissolved. The supernatant was centrifugated 15 min at 11 000 g. Pellet was than re-suspended in 20 mM potassium phosphate buffer, pH 7.5 with content of 0.5 M sodium chloride and 10 mM imidazole. The haloalkane dehalogenase was then purified on a Ni-NTA Sepharose column HR 16/10 (Qiagen, Germany). The His-tagged haloalkane dehalogenase was bound to the resin placed in the equilibrating buffer, which contained 20 mM potassium phosphate buffer pH 7.5; 0.5 M sodium chloride and 10 mM imidazole. Unbound and weakly bound proteins were washed off by buffer containing 60 mM imidazole. Then the His-tagged enzyme LinB was eluted by buffer containing 160 mM imidazole. The active fractions were dialyzed overnight against 50 mM potassium phosphate buffer, pH=7.5. The enzyme was stored at 4° C. in 50 mM potassium phosphate buffer, pH 7.5, containing 10% glycerol and 1 mM 2-mercaptoethanol to enhance long-lasting enzyme stability.

Hydrolytic dehalogenation catalyzed by haloalkane dehalogenase (wild type or modified) converts the toxic yperite into non-toxic bis(2-hydroxyethyl)sulfide. The hydrolytic dehalogenation of yperite was catalyzed by haloalkane dehalogenase at 37° C. in 50 mM phosphate buffer (pH 7.5; adjusted by addition of 1M NaOH solution). The yperite was added into reaction buffer to its final concentration of 94.3 $mg.l^{-1}$ of yperite in buffer. Reaction was initiated by addition of solution of enzyme LinB (50 mM potassium phosphate buffer pH 7.5; $1\times10^{-5}$ to $1\times10^{-4}$ $mol.l^{-1}$ of haloalkane dehalogenase LinB, 10 vol % of glycerol and 1 $mmol.l^{-1}$ 2-mercaptoethanol). Operation of haloalkane dehalogenase leads to rapid and complete decontamination of the yperite. The kinetics of reaction is shown in FIG. 1. Catalytic activity/power of haloalkane dehalogenase LinB at decontamination of yperite is $k_{cat}/K_m=6.9\ s^{-1}.mM^{-1}$.

FIG. 1 shows conversion of yperite by the use of haloalkane dehalogenase LinB. Spontaneous hydrolsis of yperite without enzyme $k_c=0.0046\ s^{-1}$ (empty circles) and degradation of yperite in the presence of haloalkane dehalogenaze LinB $k_{cat}/k_m=6.9\ s^{-1}.mM^{-1}$ (black/filled circles).

Sequence 1 and 2. Sequence of the gene linB and haloalkane dehalogenase LinB isolated from bacterium *Sphingomonas paucimobilis* UT26.

```
atg agc ctc ggc gca aag cca ttt ggc gag aag aaa
ttc att gag atc aag ggc cgg cgc atg gcc tat atc
gat gaa ggg acc ggc gat ccg atc ctc ttc cag cac
```

-continued

```
ggc aat ccg acg tcg tcc tat ctg tgg cgc aat atc
atg ccg cat tgc gcc ggg ctg gga cgg ctg atc gcc
tgt gac ctg atc ggc atg ggc gat tcg gac aag ctc
gat ccg tcg ggg ccc gag cgt tat gcc tat gcc gag
cat cgt gac tat ctc gac gcg ctg tgg gag gcg ctc
gat ctc ggg gac agg gtt gtt ctg gtc gtg cat gac
tgg ggg tcc gcc ctc ggc ttc gac tgg gcc cgc cgc
cac cgc gag cgt gta cag ggg att gcc tat atg gaa
gcg atc gcc atg ccg atc gaa tgg gcg gat ttt ccc
gaa cag gat cgc gat ctg ttt cag gcc ttt cgc tcg
cag gcg ggc gaa gaa ttg gtg ttg cag gac aat gtt
ttt gtc gaa caa gtt ctc ccc gga ttg atc ctg cgc
ccc tta agc gaa gcg gag atg gcc gcc tat cgc gag
ccc ttc ctc gcc gcc ggc gaa gcc cgt cga ccg acc
ctg tct tgg cct cgc caa atc ccg atc gca ggc acc
ccg gcc gac gtg gtc gcg atc gcc cgg gac tat gcc
ggc tgg ctc agc gaa agc ccg att ccg aaa ctc ttc
atc aac gcc gag ccg gga gcc ctg acc acg ggc cga
atg cgc gac ttc tgc cgc aca tgg cca aac cag acc
gaa atc acg gtc gca ggc gcc cat ttc atc cag gag
gac agt ccg gac gag att ggc gcg gcg att gcg gcg
ttt gtc cgg cga ttg cgc cca gca taa MSLGAKPFGEKKFIEIKGRRMAYIDEGTGDPILFQHGNPTSSYLWRNIMP
HCAGLGRLIACDLIGMGDSDKLDPSGPERYAYAEHRDYLDALWEALDLGD
RVVLVVHDWGSALGFDWARRHRERVQGIAYMEAIAMPIEWADFPEQDRDL
FQAFRSQAGEELVLQDNVFVEQVLPGLILRPLSEAEMAAYREPFLAAGEA
RRPTLSWPRQIPIAGTPADVVAIARDYAGWLSESPIPKLFINAEPGALTT
GRMRDFCRTWPNQTEITVAGAHFIQEDSPDEIGAAIAAFVRRLRPA
```

Example 2

To overproduce enzyme haloalkane dehalogenase DhaA from *Rhodococcus rhodochrous* NCIMB 13064 (Sequence 3 and 4), the corresponding gene was cloned in the pAQN vector containing tac promotor ($P_{tac}$) under the control of $lacI^q$. *Escherichia coli* BL21 containing pAQN plasmid was cultured in 250 ml Luria broth at 37° C. The induction of enzyme synthesis was initiated by addition of isopropyl-β-D-thiogalactopyranoside to a final concentration of 0.5 mM when the culture reached an optical density of 0.6 at 600 nm. After induction, the culture was incubated at 30° C. for 4 h and then harvested. The cells were disrupted by sonication using a Soniprep 150 (Sanyo, UK). The supernatant was used after centrifugation at 100 000 g for 1 h. The haloalkane dehalogenase was purified on a Ni-NTA Sepharose column HR 16/10 (Qiagen, Germany). His-tagged haloalkane dehalogenase was bound onto the resin placed in the equilibrating buffer, which contained 20 mM potassium phosphate buffer pH 7.5, 0.5 M sodium chloride and 10 mM imidazole. Unbound and weakly bound proteins were washed off by buffer containing 60 mM imidazole. The His-tagged haloalkane dehalogenase was then eluted by buffer containing 160 mM imidazole. The active fractions were dialysed overnight against 50 mM potassium phosphate buffer, pH 7.5. The enzyme was stored at 4° C. in 50 mM potassium phosphate buffer, pH 7.5, containing 10% glycerol and 1 mM 2-mercaptoethanol enhancing long-term enzyme stability.

Enzyme haloalkane dehalogenase DhaA or its variant is the part of decontamination composition that contains aforementioned enzyme at concentration $1\times10^{-6}$ to $1\times10^{-4}$ mol.l$^{-1}$, further 1 to 5 vol % of aliphatic hydrocarbon of general formula $C_nH_{2n+2}$ or cyclic aliphatic hydrocarbon of general formula $C_nH_{2n}$, where n is 6 to 12, further 5 to 20 vol % of aliphatic alcohol of general formula $C_nH_{2n+1}OH$, where n is 2 to 4, further 3 to 15 weight % of anion active tenside of general formula $C_nH_{2n+1}OSO_3Me$, where n is 10 to 16 and Me stands for counter ion (Na$^+$, K$^+$ or monoethanol amonium), 1 to 10 weight % alkylbenzenesulfonate of general formula $R^{(3)}-(Ar)SO_3^-.Me^+$, where $R^{(3)}$ stands for alkyl with 11 to 13 atoms of carbon, and Me$^+$ indicates sodium ion, further components of glycine buffer to adjust pH of aqueous solution in the range from 7 to 9, or else glycine of total concentration 0.1 mol.l$^{-1}$, etc. Required pH 8.2 is reached by addition of 1M NaOH. The rest to make 100% is water. The catalytic power of haloalkane dehalogenase DhaA at decontamination of yperite is $k_{cat}/K_m$=5.7 s$^{-1}$.mM$^{-1}$.

Sequence 3 and 4. Sequence of the gene dhaA and haloalkane dehalogenase DhaA isolated from bacterium *Rhodococcus rhodochrous* NCIMB 13064.

```
atg tca gaa atc ggt aca ggc ttc ccc ttc gac ccc
cat tat gtg gaa gtc ctg ggc gag cgt atg cac tac
gtc gat gtt gga ccg cgg gat ggc acg cct gtg ctg
ttc ctg cac ggt aac ccg acc tcg tcc tac ctg tgg
cgc aac atc atc ccg cat gta gca ccg agt cat cgg
tgc att gct cca gac ctg atc ggg atg gga aaa tcg
gac aaa cca gac ctc gat tat ttc ttc gac gac cac
gtc cgc tac ctc gat gcc ttc atc gaa gcc ttg ggt
ttg gaa gag gtc gtc ctg gtc atc cac gac tgg ggc
tca gct ctc gga ttc cac tgg gcc aag cgc aat ccg
gaa cgg gtc aaa ggt att gca tgt atg gaa ttc atc
cgg cct atc ccg acg tgg gac gaa tgg ccg gaa ttc
gcc cgt gag acc ttc cag gcc ttc cgg acc gcc gac
gtc ggc cga gag ttg atc atc gat cag aac gct ttc
atc gag ggt gcg ctc ccg aaa tgc gtc gtc cgt ccg
ctt acg gag gtc gag atg gac cac tat cgc gag ccc
ttc ctc aag cct gtt gac cga gag cca ctg tgg cga
ttc ccc aac gag ctg ccc atc gcc ggt gag ccc gcg
aac atc gtc gcg ctc gtc gag gca tac atg aac tgg
ctg cac cag tca cct gtc ccg aag ttg

```
cag cat cgc gac cga gtg cag ggg atc gcg ttc atg gaa gcg atc gtc acc ccg atg acg tgg gcg gac tgg ccg ccg gcc gtg cgg ggt gtg ttc cag ggt ttc cga tcg cct caa ggc gag cca atg gcg ttg gag cac aac atc ttt gtc gaa cgg gtg ctg ccc ggg gcg atc ctg cga cag ctc agc gac gag gaa atg aac cac tat cgg cgg cca ttc gtg aac ggc ggc gag gac cgt cgc ccc acg ttg tcg tgg cca cga aac ctt cca atc gac ggt gag ccc gcc gag gtc gtc gcg ttg gtc aac gag tac cgg agc tgg ctc gag gaa acc gac atg ccg aaa ctg ttc atc aac gcc gag ccc ggc gcg atc atc acc ggc cgc atc cgt gac tat gtc agg agc tgg ccc aac cag acc gaa atc aca gtg ccc ggc gtg cat ttc gtt cag gag gac agc cca gag gaa atc ggt gcg gcc ata gca cag ttc gtc cgg cag ctc cgg tcg gcg gcc ggc gtc tga MTAFGVEPYGQPKYLEIAGKRMAYIDEGKGDAIVFQHGNPTSSYLWRNIM
PHLEGLGRLVACDLIGMGASDKLSPSGPDRYSYGEQRDFLFALWDALDLG
DHVVLVLHDWGSALGFDWANQHRDRVQGIAFMEAIVTPMTWADWPPAVRG
VFQGFRSPQGEPMALEHNIFVERVLPGAILRQLSDEEMNHYRRPFVNGGE
DRRPTLSWPRNLPIDGEPAEVVALVNEYRSWLEETDMPKLFINAEPGAII
TGRIRDYVRSWPNQTEITVPGVHFVQEDSPEEIGAAIAQFVRQLRSAAGV
```

Example 4

Enzyme haloalkane dehalogenase LinB or its variant is the part of decontamination composition that contains the enzyme at concentrations $1\times10^{-6}$ to $1\times10^{-4}$ mol.$l^{-1}$, further 1 to 15 weight % of anion active surfactant of general formula $C_nH_{2n+1}OSO_3Me$, where n is 10 to 16 and Me stands for counter ion ($Na^+$, $K^+$ or monoethanol ammonium), 1 to 10 weight % of ethoxylated nonylphenol of general formula $C_9H_{19}$—Ar—O—$(C_2H_4O)_nH$, where n is 9 to 10, further components of phosphate buffer to adjust pH of aqueous solution in the range from 7 to 8.5; that is $KH_2PO_4$ a $K_2HPO_4$ in the required ratio and in a total concentration 50 mmol.$l^{-1}$, etc. The rest to make 100% is water.

INDUSTRIAL APPLICABILITY

This invention is utilizable in industry to eliminate yperite from the surfaces of military hardware, transportation, industrial and agricultural hardware, technical devices and constructional objects, of the human or animal skin and elements of environment, that are contaminated by this highly toxic blistering substance. This technology is utilizable in armed forces and also in civil services, generally there, where the use of detoxication compositions to decontaminate blistering substances is necessary.

SEQUENCE LISTING

```
<160> NUMBER OF SEQ ID NOS: 6

<210> SEQ ID NO 1
<211> LENGTH: 891
<212> TYPE: DNA
<213> ORGANISM: Sphingomonas paucimobilis

<400> SEQUENCE: 1
atgagcctcg gcgcaaagcc atttggcgag aagaaattca ttgagatcaa gggccggcgc    60
atggcctata tcgatgaagg gaccggcgat ccgatcctct tccagcacgg caatccgacg   120
tcgtcctatc tgtggcgcaa tatcatgccg cattgcgccg ggctgggacg gctgatcgcc   180
tgtgacctga tcggcatggg cgattcggac aagctcgatc cgtcggggcc cgagcgttat   240
gcctatgccg agcatcgtga ctatctcgac gcgctgtggg aggcgctcga tctcggggac   300
agggttgttc tggtcgtgca tgactggggg tccgccctcg gcttcgactg ggcccgccgc   360
caccgcgagc gtgtacaggg gattgcctat atggaagcga tcgccatgcc gatcgaatgg   420
gcggattttc cgaacaggat cgcgatctg tttcaggcct ttcgctcgca ggcgggcgaa   480
gaattggtgt gcaggacaa tgtttttgtc gaacaagttc tccccggatt gatcctgcgc   540
cccttaagcg aagcggagat ggccgcctat cgcgagccct tcctcgccgc cggcgaagcc   600
cgtcgaccga ccctgtcttg gcctcgccaa atcccgatcg caggcacccc ggccgacgtg   660
gtcgcgatcg cccgggacta tgccggctgg ctcagcgaaa gcccgattcc gaaactcttc   720
```

```
atcaacgccg agccgggagc cctgaccacg ggccgaatgc gcgacttctg ccgcacatgg    780
ccaaaccaga ccgaaatcac ggtcgcaggc gcccatttca tccaggagga cagtccggac    840
gagattggcg cggcgattgc ggcgtttgtc cggcgattgc gcccagcata a             891
```

<210> SEQ ID NO 2
<211> LENGTH: 296
<212> TYPE: PRT
<213> ORGANISM: Sphingomonas paucimobilis

<400> SEQUENCE: 2

```
Met Ser Leu Gly Ala Lys Pro Phe Gly Glu Lys Lys Phe Ile Glu Ile
1               5                   10                  15

Lys Gly Arg Arg Met Ala Tyr Ile Asp Glu Gly Thr Gly Asp Pro Ile
            20                  25                  30

Leu Phe Gln His Gly Asn Pro Thr Ser Ser Tyr Leu Trp Arg Asn Ile
        35                  40                  45

Met Pro His Cys Ala Gly Leu Gly Arg Leu Ile Ala Cys Asp Leu Ile
    50                  55                  60

Gly Met Gly Asp Ser Asp Lys Leu Asp Pro Ser Gly Pro Glu Arg Tyr
65                  70                  75                  80

Ala Tyr Ala Glu His Arg Asp Tyr Leu Asp Ala Leu Trp Glu Ala Leu
                85                  90                  95

Asp Leu Gly Asp Arg Val Val Leu Val Val His Asp Trp Gly Ser Ala
            100                 105                 110

Leu Gly Phe Asp Trp Ala Arg Arg His Arg Glu Arg Val Gln Gly Ile
        115                 120                 125

Ala Tyr Met Glu Ala Ile Ala Met Pro Ile Glu Trp Ala Asp Phe Pro
    130                 135                 140

Glu Gln Asp Arg Asp Leu Phe Gln Ala Phe Arg Ser Gln Ala Gly Glu
145                 150                 155                 160

Glu Leu Val Leu Gln Asp Asn Val Phe Val Glu Gln Val Leu Pro Gly
                165                 170                 175

Leu Ile Leu Arg Pro Leu Ser Glu Ala Glu Met Ala Ala Tyr Arg Glu
            180                 185                 190

Pro Phe Leu Ala Ala Gly Glu Ala Arg Arg Pro Thr Leu Ser Trp Pro
        195                 200                 205

Arg Gln Ile Pro Ile Ala Gly Thr Pro Ala Asp Val Val Ala Ile Ala
    210                 215                 220

Arg Asp Tyr Ala Gly Trp Leu Ser Glu Ser Pro Ile Pro Lys Leu Phe
225                 230                 235                 240

Ile Asn Ala Glu Pro Gly Ala Leu Thr Thr Gly Arg Met Arg Asp Phe
                245                 250                 255

Cys Arg Thr Trp Pro Asn Gln Thr Glu Ile Thr Val Ala Gly Ala His
            260                 265                 270

Phe Ile Gln Glu Asp Ser Pro Asp Glu Ile Gly Ala Ala Ile Ala Ala
        275                 280                 285

Phe Val Arg Arg Leu Arg Pro Ala
    290                 295
```

<210> SEQ ID NO 3
<211> LENGTH: 882
<212> TYPE: DNA
<213> ORGANISM: Rhodococcus rhodochrous

<400> SEQUENCE: 3

-continued

```
atgtcagaaa tcggtacagg cttcccttc gaccccatt atgtggaagt cctgggcgag      60
cgtatgcact acgtcgatgt tggaccgcgg gatggcacgc ctgtgctgtt cctgcacggt     120
aacccgacct cgtcctacct gtggcgcaac atcatcccgc atgtagcacc gagtcatcgg    180
tgcattgctc cagacctgat cgggatggga aaatcggaca aaccagacct cgattatttc    240
ttcgacgacc acgtccgcta cctcgatgcc ttcatcgaag ccttgggttt ggaagaggtc    300
gtcctggtca tccacgactg gggctcagct ctcggattcc actgggccaa gcgcaatccg    360
gaacgggtca aggtattgc atgtatggaa ttcatccggc ctatcccgac gtgggacgaa     420
tggccggaat tcgcccgtga accttccag gccttccgga ccgccgacgt cggccgagag    480
ttgatcatcg atcagaacgc tttcatcgag ggtgcgctcc cgaaatgcgt cgtccgtccg    540
cttacggagg tcgagatgga ccactatcgc gagcccttcc tcaagcctgt tgaccgagag    600
ccactgtggc gattccccaa cgagctgccc atcgccggtg agcccgcgaa catcgtcgcg    660
ctcgtcgagg catacatgaa ctggctgcac cagtcacctg tcccgaagtt gttgttctgg    720
ggcacacccg gcgtactgat ccccccggcc gaagccgcga cttgccga aagcctcccc     780 aactgcaaga cagtggacat cggcccggga ttgcactacc tccaggaaga caacccggac    840
cttatcggca gtgagatcgc gcgctggctc cccgcactct ag                       882
```

<210> SEQ ID NO 4
<211> LENGTH: 293
<212> TYPE: PRT
<213> ORGANISM: Rhodococcus rhodochrous

<400> SEQUENCE: 4

```
Met Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
                20                  25                  30

Thr Pro Val Leu Phe Leu His Gly Asn Pro Thr Ser Ser Tyr Leu Trp
            35                  40                  45

Arg Asn Ile Ile Pro His Val Ala Pro Ser His Arg Cys Ile Ala Pro
        50                  55                  60

Asp Leu Ile Gly Met Gly Lys Ser Asp Lys Pro Asp Leu Asp Tyr Phe
65                  70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
                100                 105                 110

Phe His Trp Ala Lys Arg Asn Pro Glu Arg Val Lys Gly Ile Ala Cys
            115                 120                 125

Met Glu Phe Ile Arg Pro Ile Pro Thr Trp Asp Glu Trp Pro Glu Phe
130                 135                 140

Ala Arg Glu Thr Phe Gln Ala Phe Arg Thr Ala Asp Val Gly Arg Glu
145                 150                 155                 160

Leu Ile Ile Asp Gln Asn Ala Phe Ile Glu Gly Ala Leu Pro Lys Cys
                165                 170                 175

Val Val Arg Pro Leu Thr Glu Val Glu Met Asp His Tyr Arg Glu Pro
            180                 185                 190

Phe Leu Lys Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Ala
    210                 215                 220
```

Tyr Met Asn Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
            245                 250                 255

Glu Ser Leu Pro Asn Cys Lys Thr Val Asp Ile Gly Pro Gly Leu His
        260                 265                 270

Tyr Leu Gln Glu Asp Asn Pro Asp Leu Ile Gly Ser Glu Ile Ala Arg
    275                 280                 285

Trp Leu Pro Ala Leu
    290

<210> SEQ ID NO 5
<211> LENGTH: 903
<212> TYPE: DNA
<213> ORGANISM: Mycobacterium bovis

<400> SEQUENCE: 5
atgacagcat tcggcgtcga gccctacggg cagccgaagt acctagaaat cgccgggaag    60
cgcatggcgt atatcgacga aggcaagggt gacgccatcg tctttcagca cggcaacccc   120
acgtcgtctt acttgtggcg caacatcatg ccgcacttgg aagggctggg ccggctggtg   180
gcctgcgatc tgatcgggat gggcgcgtcg gacaagctca gcccatcggg acccgaccgc   240
tatagctatg gcgagcaacg agactttttg ttcgcgctct gggatgcgct cgacctcggc   300
gaccacgtgg tactggtgct gcacgactgg ggctcggcgc tcggcttcga ctgggctaac   360
cagcatcgcg accgagtgca ggggatcgcg ttcatggaag cgatcgtcac cccgatgacg   420
tgggcggact ggccgccggc cgtgcggggt gtgttccagg gtttccgatc gcctcaaggc   480
gagccaatgg cgttggagca caacatcttt gtcgaacggg tgctgcccgg ggcgatcctg   540
cgacagctca gcgacgagga aatgaaccac tatcggcggc cattcgtgaa cggcggcgag   600
gaccgtcgcc ccacgttgtc gtggccacga aaccttccaa tcgacggtga gcccgccgag   660
gtcgtcgcgt tggtcaacga gtaccggagc tggctcgagg aaaccgacat gccgaaactg   720
ttcatcaacg ccgagcccgg cgcgatcatc accggccgca tccgtgacta tgtcaggagc   780
tggcccaacc agaccgaaat cacagtgccc ggcgtgcatt tcgttcagga ggacagccca   840
gaggaaatcg gtgcggccat agcacagttc gtccggcagc tccggtcggc ggccggcgtc   900
tga                                                                 903

<210> SEQ ID NO 6
<211> LENGTH: 300
<212> TYPE: PRT
<213> ORGANISM: Mycobacterium bovis

<400> SEQUENCE: 6

Met Thr Ala Phe Gly Val Glu Pro Tyr Gly Gln Pro Lys Tyr Leu Glu
1               5                   10                  15

Ile Ala Gly Lys Arg Met Ala Tyr Ile Asp Glu Gly Lys Gly Asp Ala
            20                  25                  30

Ile Val Phe Gln His Gly Asn Pro Thr Ser Ser Tyr Leu Trp Arg Asn
        35                  40                  45

Ile Met Pro His Leu Glu Gly Leu Gly Arg Leu Val Ala Cys Asp Leu
    50                  55                  60

Ile Gly Met Gly Ala Ser Asp Lys Leu Ser Pro Ser Gly Pro Asp Arg
65                  70                  75                  80

-continued

```
Tyr Ser Tyr Gly Glu Gln Arg Asp Phe Leu Phe Ala Leu Trp Asp Ala
            85                  90                  95

Leu Asp Leu Gly Asp His Val Val Leu Val Leu His Asp Trp Gly Ser
            100                 105                 110

Ala Leu Gly Phe Asp Trp Ala Asn Gln His Arg Asp Arg Val Gln Gly
            115                 120                 125

Ile Ala Phe Met Glu Ala Ile Val Thr Pro Met Thr Trp Ala Asp Trp
            130                 135                 140

Pro Pro Ala Val Arg Gly Val Phe Gln Gly Phe Arg Ser Pro Gln Gly
145                 150                 155                 160

Glu Pro Met Ala Leu Glu His Asn Ile Phe Val Glu Arg Val Leu Pro
            165                 170                 175

Gly Ala Ile Leu Arg Gln Leu Ser Asp Glu Glu Met Asn His Tyr Arg
            180                 185                 190

Arg Pro Phe Val Asn Gly Gly Glu Asp Arg Arg Pro Thr Leu Ser Trp
            195                 200                 205

Pro Arg Asn Leu Pro Ile Asp Gly Glu Pro Ala Glu Val Val Ala Leu
210                 215                 220

Val Asn Glu Tyr Arg Ser Trp Leu Glu Glu Thr Asp Met Pro Lys Leu
225                 230                 235                 240

Phe Ile Asn Ala Glu Pro Gly Ala Ile Ile Thr Gly Arg Ile Arg Asp
            245                 250                 255

Tyr Val Arg Ser Trp Pro Asn Gln Thr Glu Ile Thr Val Pro Gly Val
            260                 265                 270

His Phe Val Gln Glu Asp Ser Pro Glu Glu Ile Gly Ala Ala Ile Ala
            275                 280                 285

Gln Phe Val Arg Gln Leu Arg Ser Ala Ala Gly Val
            290                 295                 300
```

The invention claimed is:

1. Method of detoxification of yperite comprising treating said yperite with at least one haloalkane dehalogenase, at an enzyme concentration of $1 \times 10^{-6}$ to $1 \times 100$ mol.l$^{-1}$, at temperature from +10° C. to +70° C. and pH from 4 to 12 in liquid medium,
wherein the haloalkane dehalogenase is an enzyme selected from the group consisting of dehalogenases LinB from *Sphingomonas paucimobilis* UT26 (SEQ ID NO: 2), DhaA from *Rhodococcus rodochrous* NCIMB 13064 (SEQ ID NO: 4), and DmbA from *Mycobacterium bovis* 5033/66 (SEQ ID NO: 6).

2. Method according to claim 1, wherein the liquid medium is an organic solvent, a mono-phasic aqueous solution of organic solvent or bi-phasic system consisting of organic solvent and water.

3. Method according to claim 2, wherein the haloalkane dehalogenase solution includes a buffer system.

4. Method according to claim 1, wherein the preparation of haloalkane dehalogenase is carried out in the presence of at least one protein stabilizer, selected from the group consisting of polyalcohols, inactive proteins, polymers.

5. Method according to claim 1, wherein the enzyme haloalkane dehalogenase is used as soluble form or as crystalline form or as lyophilized form or as precipitated form.

6. Method according to claim 1, wherein the enzyme haloalkane dehalogenase is immobilized by adsorption, by ionic binding or by covalent attachment onto the surface of organic or inorganic carrier.

7. Method according to claim 1, wherein the enzyme haloalkane dehalogenase is immobilized by cross-linking or entrapping enzyme into a solid matrix or a compartment confined by a membrane.

8. Method according to claim 1, wherein the detoxification is carried out in the presence of surfactants.

* * * * *